US00PP18375P2

(12) United States Plant Patent
Berry

(10) Patent No.: US PP18,375 P2
(45) Date of Patent: Jan. 1, 2008

(54) ***LOROPETALUM* PLANT NAMED 'PLAZE'**

(50) Latin Name: *Loropetalum chinensis*
Varietal Denomination: Plaze

(76) Inventor: James Bryan Berry, 25075 Austin Rd., Daphne, AL (US) 36526

( * ) Notice: Subject to any disclaimer, the term of this patent is extended or adjusted under 35 U.S.C. 154(b) by 0 days.

(21) Appl. No.: 11/297,140

(22) Filed: Dec. 8, 2005

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—June Hwu

(57) ABSTRACT

A new and distinct variety of *Loropetalum* that possesses unique color and growth habit.

1 Drawing Sheet

Latin name: *Loropetalum chinensis.*
Variety denomination: 'Plaze'.

BACKGROUND OF THE INVENTION

The present invention relates to a new and distinct variety of *Loropetalum chinensis,* which was discovered as an unusual, distinctive, and ornamentally special seedling of unpatented *Loropetalum chinensis* 'Pizzazz™' at a commercial greenhouse located close to Loxley, Ala., by James Bryan Berry in 2002. The unique characteristics of the new variety 'Plaze' will make the plant useful when used as a groundcover in the landscape in appropriate USDA climactic zones. The plant is unlike the species in growth habit.

*Loropetalum chinensis* 'Plaze' has been asexually reproduced for four generations by cutting and has demonstrated stability of growth of all phenotypic characteristics from the original plant thru each generation. Asexually reproduction was achieved at a commercial greenhouse in Loxley, Ala. by James Bryan Berry. Thru this propagation process the variety 'Plaze' has been reliably stable and true to type for several generations.

BRIEF DESCRIPTION OF ILLUSTRATION

FIG. 1 Demonstrates the density of growth and intensity of color.

FIG. 2 Demonstrates the unusually dark pigmentation of the leaf topside and underside.

DETAILED BOTANICAL DESCRIPTION OF THE PLANT

Color references are made to The Royal Horticultural Society Colour Chart (1995 Edition) and all terminology used is from this color chart. Otherwise descriptive terminology is botanic or ordinary in nature. Plants grown in #3 containers were used for the following descriptions as grown under normal, commercial conditions near Loxley, Ala. During the production period day temperatures ranged from 29 to 37 degrees Celsius and night temperatures ranged from 25 to 27 degrees Celsius. This botanic description was made in November 2005. Observations were made and date collected from a three (3) year old plant.

Botanical: *Loropetalum chinensis* 'Plaze'.
Parentage: Seedling of non-patented *Loropetalum chinensis* 'Pizzazz™'.
Propagation: By vegetative cutting.
Time to initiate roots, summer: 14-20 days at 28° Celsius.
Time to initiate roots, winter: 32-40 days at 20° Celsius.
Time to produce a rooted plant, summer: About 5 months at 28° Celsius.
Time to produce a rooted plant, winter: About 7 months at 28° Celsius Plant Hardy to Zone 7.
Roots: Dark red and branching, not fibrous, fleshy.
General appearance: Dark brown foliage, densely branching.
Size: 4' tall and 4' wide.
Branching: Dense.
Lateral branches: Multi-branched shrub.
Branch length: Averages 20" long.
Habit: Globose.
Hardiness: USDA Zone 7.
Vigor: Average.
Pests/diseases: No pest or disease problems noted.
Flower: Perfect, Red-Purple Group 61A (upper surface and under surface), glabrous, four strap-shaped petals. The flowers form a loose funnel, are borne on current season's growth, and are non-fragrant; they last on the plant in the garden five to seven days. Tight buds at 3/16 inch are orbicular, Red-Purple Group 63B and pubescent. Six to eight flowers form globose heads on branchlet terminals and occasionally one to two flowers in the leaf axils. Flowering occurs from early March to late March with light repeat blooming throughout the growing season. These racemes are 1¼ inches to 1½ inches in diameter by 5/8 inch to 7/8 inch in depth and abundantly cover the plant. The flowers are attached in a circular pattern to short peduncles which are pubescent, 1/16 inch long, 1/32 inch in diameter ad Red-Purple Group 63B. The four petals which arise from the calyx tube at the sepal base are linear, crinkled, 5/8 inch to 7/8 inch long, 1/16 inch to 1/8 inch wide, with retuse apexes and entire margins. There are four stamens 1/32 inch long, Red-Purple Group 63A, with anthers also Red-Purple Group 63A. Pollen matures to Yellow-Green Group 11D and is produced in very small amounts. The two pistils are 1/32 inch long and Red-Purple Group 63A. The ovary is inferior and two-celled. Each flower has four sepals that have entire revolute margins which are 1/16 inch long, 1/16 inch wide, ovate, and fused into a calyx. The calyx is 3/16 inch in diameter, 3/16 inch in depth, pubescent and Red-Purple Group 63B outer surface and Red-Purple Group 63A inner surface.

Fruit: Woody, scabrous, ovoid, 3/16 inch to 5/16 inch long, 1/8 inch to 1/4 inch in diameter, two celled capsule, one seed per cell. Mature plants produce 75 to 100 fruits which are Yellow-Green Group 146B. Seeds are 1/8 inch long, 1/16 inch to 1/8 inch in diameter, Brown Group 200C, and mature in the fall.

Leaf:

*Margin.*—Entire with stellate hairs.

*Venation.*—Pinnate.

*Shape.*—Ovate.

*Arrangement.*—Alternate, simple.

*Apex.*—Acute.

*Leaf base.*—Acute.

*Texture.*—Upper and lower, pubescent and coarse, non-pliable, impressed veins, underside glacous. Midribs and veins with stellate hairs.

*Color and top.*—Brown Group 200A.

*Underside.*—Brown Group 187D.

*Vein and midrib.*—Grayed purple group 185D.

*Petioles.*—The petioles are 1/8 inch to 3/16 inch long, 1/32 inch in diameter, heavily stellate-pubescent and Greyed-Purple Group 187B.

*Stem.*—The young stems are Greyed-Purple Group 187A and heavily stellate-pubescent. During the second growing season they become Brown Group 200C. The pith is solid and uniform. Young and older stems are densely branched.

Disease and insect resistance: Resistance to disease and insects common to plants of *Loropetalum* have not been observed.

Other Data Provided

Comparison with Parent

*Loropetalum chinensis* 'Plaze' is unique in growth habit. A four-year-old plant is naturally 4 feet tall and 4 feet wide without pruning or shaping. The plant is strongly globose. The parent variety *Loropetalum chinensis* 'Pizzazz™' is not compact but is an upright growing shrub to about 12 feet high and 7 feet wide.

'Plaze' is distinctive to another known cultivars because the underside of the leaf is a deep violet. The parent *Loropetalum chinensis* 'Pizzazz™' as well as 'Bill Wallace', U.S. Plant Pat. No. 15,277 all have leaves with undersides that are green.

Comparison to Comparable Cultivars

The following traits are determined to be the unique characteristics of 'Plaze'. The traits which cause 'Plaze' to be a new and distinct cultivar are:

1. Deep, violet (non-green) pigmentation of underside of leaf
2. Globose and dwarfed growth habit.

In side-by-side comparisons, plants of the new *Loropetalum chinensis* 'Plaze' differed from plants of the cultivar 'Bill Wallace' in the following ways:

1. Plants of the new cultivar 'Plaze' are globose compared to 'Bill Wallace' which is outwardly spreading with prostrate plant growth.
2. Leaves of the new cultivar 'Plaze' are larger and wider compared to the leaves of 'Bill Wallace', which are narrow and small.
3. The underneath side of the leaves of 'Plaze' are deep violet and the underneath sides of the leaves of 'Bill Wallace' are green.

In side-by-side comparisons, plants of the new *Loropetalum chinensis* 'Plaze' differed from the non-patented parent cultivar, 'Pizzazz™' in the following ways:

1. Plants of the new cultivar 'Plaze' are globose compared to 'Pizzazz™' which grows strongly upright.
2. The underneath side of the leaves of 'Plaze' are deep violet and the underneath sides of the leaves of 'Pizzazz™' are green.

In side-by-side comparisons, plants of the new *Loropetalum chinensis* 'Plaze' differed from the patented cultivar 'ZhuZhou' in the following way:

1. Plants of the new cultivar 'Plaze' are globose compared to 'ZhuZhou', which grows strongly upright.

SUMMARY OF THE INVENTION

*Loropetalum chinensis* 'Plaze' has a unique combination of characteristics. 'Plaze' has dense branching with deep purple foliage pigmentation. 'Plaze' is an intermediate growing broadleaf evergreen ornamental shrub that should be used in the landscape for mass plantings when low maintenance, low hedging plants with foliage color are desirable.

It is claimed:

1. A new and unique variety of *Loropetalum* named 'Plaze' as herein shown and described.

* * * * *

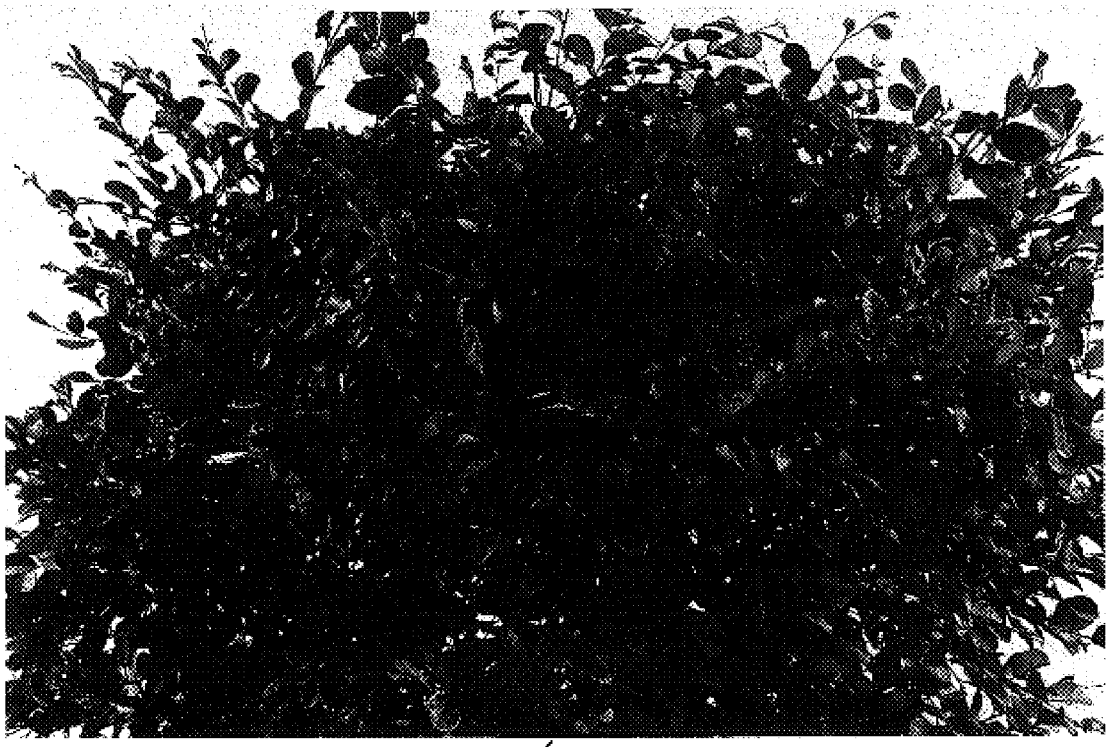
figure one
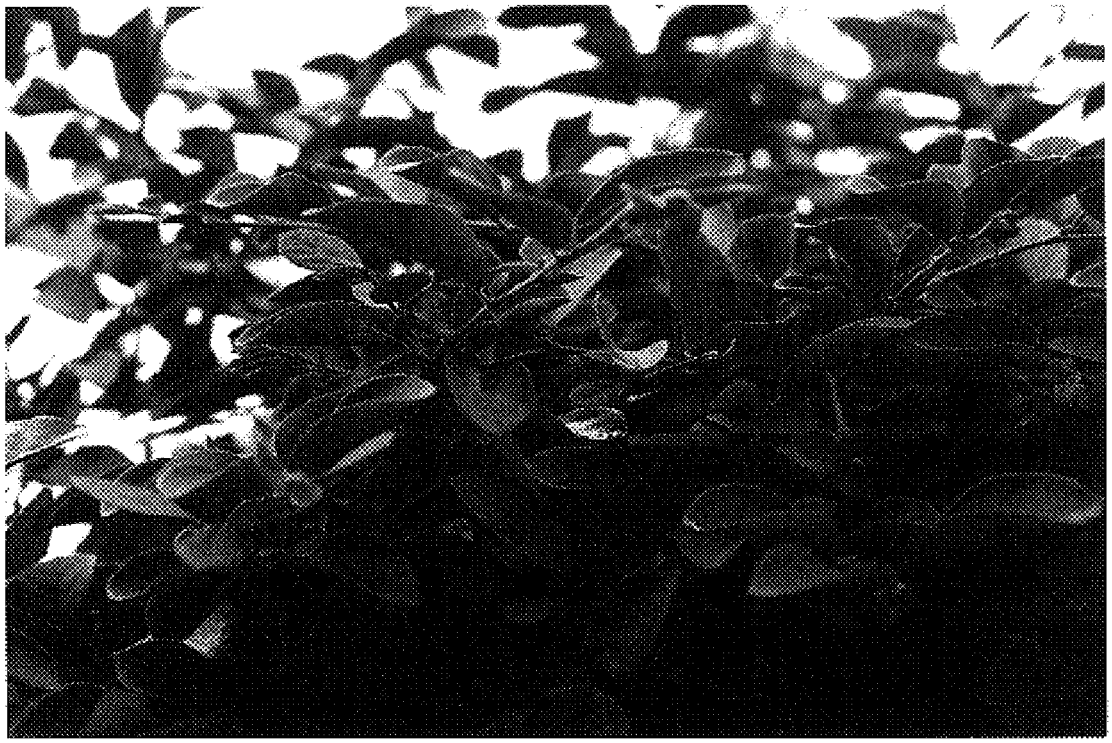
figure two